United States Patent
Fhölenhag et al.

[11] Patent Number: 5,872,097
[45] Date of Patent: Feb. 16, 1999

[54] OLIGOPEPTIDES WITH AFFINITY TO OPIOID RECEPTORS

[75] Inventors: Karin Ingeborg Fhölenhag, Bromma; Linda Fryklund, Sollentuna; Bo Christer Larsson; Fred Jarl Nyberg, both of Upsala; Gertrud Elisabeth Westin-Sjödahl, Södertälje; Ronny Lundin, Ekerö, all of Sweden

[73] Assignee: Pharmacia & Upjohn Aktiebolag, Stockholm, Sweden

[21] Appl. No.: 433,401

[22] PCT Filed: Nov. 8, 1993

[86] PCT No.: PCT/SE93/00986

§ 371 Date: Sep. 7, 1995

§ 102(e) Date: Sep. 7, 1995

[87] PCT Pub. No.: WO94/12532

PCT Pub. Date: Jun. 9, 1994

[30] Foreign Application Priority Data

Nov. 20, 1992 [SE] Sweden .................... 9203496

[51] Int. Cl.⁶ .................... A61K 38/08; A61K 38/12; C07K 7/00
[52] U.S. Cl. .................... 514/9; 514/11; 514/17; 530/317; 530/318; 530/323; 530/330
[58] Field of Search .................... 514/9, 11, 17; 530/317, 318, 323, 330

[56] References Cited

U.S. PATENT DOCUMENTS

| | | | |
|---|---|---|---|
| 4,254,024 | 3/1981 | Stewart et al. | 260/112.5 |
| 4,699,897 | 10/1987 | Jones et al. | 514/4 |

FOREIGN PATENT DOCUMENTS 30 34 897 A1 of 1981 Germany .
WO 84/04915 of 1984 WIPO .

OTHER PUBLICATIONS

Chemical Abstract No. 100:115141, Vanderlaan et al., J. Protein Chem. 2(4) 341–6. (1983).
Chemical Abstract No. 75:20997., Kovacs et al., Int. J. Protein Res. 3(2) 93–8 (1971).
Björk et al., Quality of Life of Adults with Growth Hormone Deficiency: A Controlled Study, Acta Paediatr. Scand. (Suppl.) vol. 356 (1989) p. 55.
McGauley, Quality of Life Assessment Before and After Growth Hormone Treatment in Adults with Growth Hormone Deficiency, Acta Paediatr. Scand. (Suppl.) vol. 356 (1989) p. 70.
Nyberg et al., Enzymatic Release of Peptide Fragments from Human Growth Hormone which Displace ($^3$H)–Dihydromorphine from Rat Brain Opioid Receptors, Abstract, Brain Res., vol. 259 (1983), pp. 267–274 (Abstract).
Schiller et al., Conformationally Restricted Deltorphin Analogues, J. Med. Chem., vol. 35 (1992), pp. 3956–3961.
Glamsta et al., Isolation and characterization of a hemoglobin–derived opioid peptide from the human pituitary gland, Regulatory Peptides, vol. 34 (1991), pp. 169–179.
Loukas et al., Selective δ–Antagonist Peptides, Analogs of α–Casein Exorphin, as Probes for the Opioid Receptor, β–Casmorphins and Related Peptides 1990, Fyris–Tryck AB, Uppsala, Sweden.
Kovacs et al., Human Pituitary Growth Hormone.* XXV, Int. J. Protein Research III, 1971, pp. 93–98.

*Primary Examiner*—Cecilia J. Tsang
*Assistant Examiner*—Bennett Celsa
*Attorney, Agent, or Firm*—Pollock, Vande Sande & Amernick

[57] ABSTRACT

Straight or cyclic pentapeptides with receptor affinity to μ or δ opioid receptors having a primary sequence backbone of Tyr-X-Phe-Leu-Z, Seq. ID Nos. 1, 2, and 3. X and Z can be covalently coupled to provide a heterocyclic structure according to the following conditions:

i) when the pentapeptide is straight X is selected from the group consisting of Ser, Gly, Pro, AMCA and D-Ala and Z is selected from the group consisting of Glu, Gln or amino derivatives of Glu or Gln, Seq. ID No. 1, with the proviso that if X is Ser, then Z is Glu or amino derivatives of Glu; and ii) where the pentapeptide is cyclic X is selected from the group consisting of D- or L-2,4-diaminobutyric acid, D- or L-lysine, D- or L-ornithine and D or L-cysteine and Z is selected from the group consisting of Gln or Glu or amino derivatives of Gln or Glu, Seq. ID No. 2, and 3, with the proviso that if X is D-or L-Cys, then Z is Cys, Seq. ID No. 3.

8 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /product="OTHER"
            / label= Xaa
            / note= "Xaa at position 2 is Ser, Gly, Pro,
            ( t r a n s - ( 4- aminomethyl)-cyclohexan
            carboxylic acid) or D-Ala when the peptide is linear"

( i x ) FEATURE:
        ( A ) NAME/KEY: Modified-site
        ( B ) LOCATION: 5
        ( D ) OTHER INFORMATION: /product="OTHER"
            / label= Xaa
            / note= "Xaa at positon 5 is Glu, Gln or their derivatives
            when the peptide is linear"

( x i ) SEQUENCE DESCRIPTION: SEQ ID NO:1:

T y r   X a a   P h e   L e u   X a a
    1                                         5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS:

(D) TOPOLOGY: circular (i i) MOLECULE TYPE: peptide (i x) FEATURE:
            (A) NAME/KEY: Modified-site
            (B) LOCATION: 2
            (D) OTHER INFORMATION: /product="OTHER"
                    / label= Xaa
                    / note= "Xaa at positon 2 is Dbu, D-Dbu, Lys, D-Lys, Orn
                        or D- Orn when the peptide is circular"

(i x) FEATURE:
            (A) NAME/KEY: Modified-site
            (B) LOCATION: 5
            (D) OTHER INFORMATION: /product="OTHER"
                    / label= Xaa
                    / note= "Xaa at position 5 is Glu, Gln or their amino
                        derivatives when the peptide is circular"

(x i) SEQUENCE DESCRIPTION: SEQ ID NO:2:

Tyr   Xaa   Phe   Leu   Xaa
    1                             5

(2) INFORMATION FOR SEQ ID NO:3:

(i) SEQUENCE CHARACTERISTICS:
            (A) LENGTH: 5 amino acids
            (B) TYPE: amino acid
            (C) STRANDEDNESS:
            (D) TOPOLOGY: circular (i i) MOLECULE TYPE: peptide (i x) FEATURE:
            (A) NAME/KEY: Disulfide-bond
            (B) LOCATION: 2
            (D) OTHER INFORMATION: /product="OTHER"
                    / label= Xaa
                    / note= "Xaa is Cys or D-cys and forms a disulfide-bond
                        with the Cys at position 5"

(x i) SEQUENCE DESCRIPTION: SEQ ID NO:3:

Tyr   Xaa   Phe   Leu   Cys
    1                             5

(2) INFORMATION FOR SEQ ID NO:4:

(i) SEQUENCE CHARACTERISTICS:
            (A) LENGTH: 4 amino acids
            (B) TYPE: amino acid
            (C) STRANDEDNESS:
            (D) TOPOLOGY: linear (i i) MOLECULE TYPE: peptide (x i) SEQUENCE DESCRIPTION: SEQ ID NO:4:

Tyr   Gly   Leu   Leu
    1

OLIGOPEPTIDES WITH AFFINITY TO OPIOID RECEPTORS

This application is a 371 of PCT/SE93/00986 Nov. 8, 1993.

FIELD OF THE INVENTION

The invention relates to new oligopeptides SEQ. ID NOS. 1, 2, and 3 with opioid receptor affinity. The peptides can be straight or cyclic pentapeptides with a primary sequence backbone Tyr-X-Phe-Leu-Z. X and Z denote amino acids or amino acid derivatives and/or analogs. X and Z can be covalently coupled to provide a heterocyclic structure. Z is chosen among Cys, Glu, Gln or derivatives of Glu and Gln. X is chosen among amino acids or amino acid analogs such as Ser, Pro, Gly, D-Ala, D- or L-2,4-diaminobutyric acid, trans-(4-aminomethyl)-cyclohexan carboxylic acid (AMCA), Cys or derivatives thereof.

The invention is also directed to pharmaceutical preparations containing the new oligopeptides, which are potentially useful as analgesics for alleviating pain, for increasing the comfort for individuals suffering from extraordinary stress or shock, for reducing depression, and for the possible treatment of individuals addicted to opiates.

BACKGROUND OF THE INVENTION

The physicians treating growth hormone deficient (GHD) patients with human growth hormone have frequently reported that patients experience an increased quality of life in comparison with a control group not subjected to the treatment. Statistically significant differences were found between the groups regarding social isolation, physical mobility, sleep and emotional status (see Acta Paed Scand (Suppl), v356, p55–59, 1989, S Björk et al. and Acta Paed Scand (Suppl), v356, p70–72, 1989, G A McCauley) In clinical treatment with human growth hormone some secondary effects on the central nervous system (CNS) have been observed. It has been suggested that opioid active peptide fragments released from growth hormone may reach the CNS if the human plasma contains proteolytic activity for releasing them. If such fragments can pass through the blood-brain barrier, they may affect the CNS. These previous studies indicate that human growth hormone affects the CNS and suggests that enzymatically released fragments may interfere with opioid receptors.

A number of studies have shown that enzymatically treated preparations of proteins can include peptides with opioid activity such as β-casomorphin, cytochrophins and hemomorphins. β-casomorphin originates from degraded beta-casein peptone and is previously disclosed in Physiol Chem, v360, p 1211–16, 1979, V Brandl et al.; Pharmacol Sci, v4, p193, 1979, V Brantl et al.; Eur J Pharmacol, v106, p213–214, 1984, V Brantl et al. and J Clin Endocrinol Metab, v68, p283–9, 1989, F Nyberg et al.

It has also been shown that enzymatically derived fragments of mitochondrial cytochrome b contain cytochrophins, another opioid peptide (see Eur J Pharmacol, v111, p293, 1985, V Brantl et al). For a reference of hemomorphins see Eur J Pharmacol, 125, p 309–10,1986, V Brantl et al. The opioid activity of these peptides were confirmed by testing their inhibition of the electrically induced contractions of the guinea-pig ileum myentric plexus longitudinal muscle preparation (GPI-assay) as well as by receptor assay.

Certain cyclic oligopeptides with opioid receptor activity have previously been disclosed by J De Maio et al. in Proc. Natl. Acad. Sci., Vol. 77(12), 1980, p 7162–6. This article discloses a number of prepared cyclic enkephalin analogs. Cyclic oligopeptides with opioid receptor affinity are also disclosed in J Med Chem, Vol. 35, 1992, p 3956–3961, P Schiller et al. U.S. Pat. No. 4,254,024 (J. Stewart et al.) discloses a class of tetrapeptides demonstrated to have opiate activity with a guinea pig ileum strip test having the general formula H-Tyr-X-Y-Z. Another reference that discloses opioid receptor binding straight tetrapeptides is European patent application EP 350 221.

In a previous study, two different peptidases were investigated for their ability to release fragments of human growth hormone, which may interfere with opioid receptors. The enzymes were a commercially available trypsin and an endopeptidase partially purified from human plasma. The fragments were separated on reversed phase HPLC and subsequently analyzed by an opioid receptor assay performed with synaptic plasma membranes from rat brains (without cerebellum). The results indicated that receptor active fragments were released both by trypsin and the endopeptidase. However, in a guinea-pig ileum myenteric plexus/longitudinal muscle preparation (GPI) assay, these fragments were found to be less potent than beta-casomorphins (fragments of casein peptone). These findings were published at the IV Meeting of the European Neuroendocrine Association (Santiago de Compostela 28–30 Jun. 1989).

Figure 1:
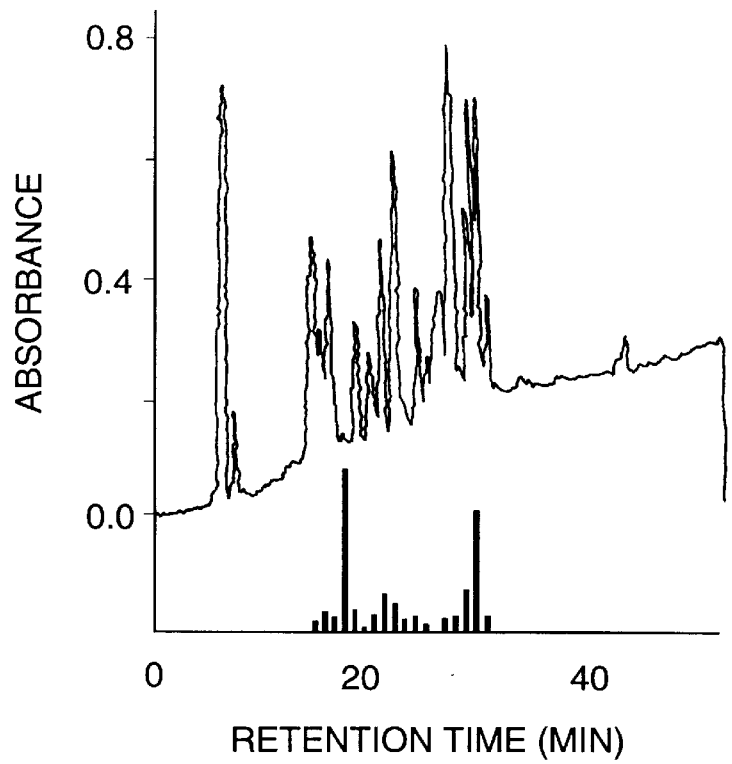
FIG. 1 shows a typical HPLC-diagram of a tryptic digest of human growth hormone (CRESCORMON®). The distribution of opioid receptor activity is represented by dark bars.

Table 1 presents initial binding data for an oligopeptide according to the present invention in comparison with β-casomorphin.

Table 2 presents opioid receptor affinity and activity assays for oligopeptides according to the present invention in comparison to prior art tetrapeptides.

DESCRIPTION OF THE INVENTION

When the sequences of the peptides obtained from tryptic digest of human growth hormone were examined, it was noticed that some subsequences in certain aspects were related to those of beta-casomorphin. These new oligopeptides with a proposed opioid activity were tetra- or pentapeptides with the sequences Tyr-Gly-Leu-Leu SEQ. ID NO. 4 and Tyr-Ser-Phe-Leu-Gln SEQ. ID NO. 1. The oligopeptides were synthesized and somewhat modified in that Gln is substituted for Glu in the pentapeptide. The peptides were subsequently tested for their opioid receptor affinity in comparison with β-casomorphin (see Table 1 below). The tests showed surprisingly, that the new oligopeptide Tyr-Ser-Phe-Leu-Glu SEQ. ID NO. 1 have an opioid receptor affinity of about the same magnitude as β-casomorphin.

This result has consequently lead to a wider scope of new oligopeptides that are straight or cyclic analogues of Tyr- Ser-Phe-Leu-Glu. These new peptides are surprisingly shown to have high affinity to opioid receptors when compared to structurally related tetrapeptides disclosed by the above-mentioned U.S. Pat. No. 4,254,024 (see also Table 2 below).

The present invention is directed to new oligopeptides with opioid receptor affinity that are derived from sequences naturally occurring in human growth hormone. The new oligopeptides are described by the general formula Tyr-X-Phe-Leu-Z, SEQ. ID NOS. 1, 2, and 3 wherein X and Z denotes amino acids, derivatives or analogues thereof, wherein X and Z can be covalently linked to form the cyclic compounds:

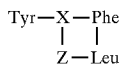

If the oligopeptide is straight, X is Ser, Gly, Pro, AMCA (trans-(4-aminomethyl)-cyclohexan carboxylic acid) or D-Ala and Z is Glu or Gln or their amino derivatives SEQ. ID NO. 1.

Some preferred straight oligopeptides according to the invention are Tyr-Ser-Phe-Leu-Glu, Tyr-Ser-Phe-Leu-Glu-NH$_2$, Tyr-D-Ala-Phe-Leu-Glu, Ty-D-Ser-Phe-Leu-Glu, Tyr-Pro-Phe-Leu-Glu, Tyr-Ser-Phe-Leu-Gln and Tyr-AMCA-Phe-Leu-Glu SEQ. ID NO. 1. The straight oligopeptides are readily prepared according to the examples below.

The cyclic oligopeptides of the present invention will be cyclizized either by a side chain of an amino acid or by oxidation of two cysteine groups. To obtain analogs to Tyr-Ser-Phe-Leu-Glu with cyclic structures amino acid number two, serine, will be substituted by D- or L-2,4-diaminobutyric acid (D- or L-Dab), D- or L-ornithine, D- or L-lysine or D- or L-cysteine. Amino acid number five can be substituted by glutamine, glutamic acid or their amino derivatives or cysteine.

In the general cyclic formula

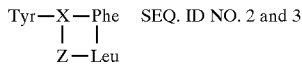

SEQ. ID NO. 2 and 3 the following amino acids will be used according to the present invention:

X=D- or L-2,4-diaminobutyric acid(D or L-Dab),D-Orn, D- or L-Lys or D- or L-Cys and Z=Glu, Gln or their amino derivatives SEQ. ID NO. 2 or Cys with the proviso that if X=D- or L-Cys then Z=Cys.

Preferred cyclic oligopeptides according to the present invention are:

Tyr-cyclo-(-Lys-Phe-Leu-Glu-) SEQ. ID NO. 2 with a peptide bond between alpha carboxy group of glutamic acid and the epsilon amino group of lysine, Tyr-cyclo(-N$^4$-2,4-D-diaminobutyric acid-Phe-Leu-Gln-) SEQ. ID NO. 2, Tyr-cyclo(-N$^4$-2,4-L-diaminobutyric acid-Phe-Leu-Gln-) SEQ. ID NO. 2, Tyr-cyclo(-N$^4$-2,4-D-diaminobutyric acid-Phe-Leu-Glu-) SEQ. ID NO. 2, Tyr-cyclo(-N$^4$-2,4-L-diaminobutyric acid-Phe-Leu-Glu-) SEQ. ID NO. 2, Tyr-cyclo(-D-Lys-Phe-Leu-Glu-) SEQ. ID NO. 2, Tyr-cyclo (-D-Orn-Phe-Leu-Glu-) SEQ. ID NO. 2, Tyr-cyclo-(D-Dab-Phe-Leu-Glu-) SEQ. ID NO. 2, Tyr-cyclo-(D-Dab-Phe-Leu-Gln-) SEQ. ID NO. 2 and the cyclic peptides.

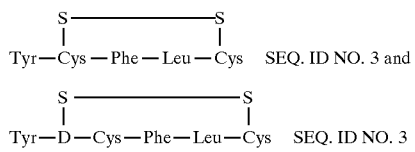

SEQ. ID NO. 3 which are cyclicized by oxidation of the two cysteine groups.

The cyclic oligopeptides have heterocyclic structure related to enkephalins and those cyclic peptides described by J De Maio et. al., in the above mentioned article.

The tests disclosed in Example 3 and Tables 1 and 2 clearly demonstrate that the oligopeptides according the present invention have a high affinity to opioid receptors and especially to the μ- and δ-receptors. Table 2 also demonstrates that the cyclic oligopeptides are functional agonists and have a high biological activity as opioids when measured on stimulated guinea pig ileum strips in relation to normorphine.

The straight peptides show, in comparison to the cyclic peptides, a considerably lower biological activity, which may give them properties to act as potential partial opioid receptor agonists or under certain circumstances as antagonists. It is notable that the biological activity of the straight peptides is considerably reduced even for those with high binding affinity profiles to the μ-receptor. The suggested partial agonists would inhibit the agonistic responses of normorphine and the cyclic peptides in equivalence with functional antagonists.

The straight and cyclic oligopeptides according to the present invention represent a new possibility for preparing drugs for alleviating pain as an analgesic, for increasing comfort for patients suffering from shock or stress or for treating depressions, for administration to individuals suffering from disorders in the levels of endogenous morphine and opiate analogues or potentially for the treatment individuals addicted to opiates. The person skilled in the art will readily find additional pharmacological uses of selected oligopeptides according to the present invention that are linked to their properties as agonists, partial agonists or antagonists to the opioid receptors.

Several administration forms of the new oligopeptides are conceivable. Both oral, transdermal and/or parenteral administration forms with appropriate carriers and/or diluents and conventionally used stabilizers and enhancers can be prepared.

The new oligopeptides will readily be formulated and modulated to suitable administration forms such as oral, nasal, parenteral, enteral or buccal preparations.

Various modifications of the invention and equivalents, such as salts and derivatives of the inventive oligopeptides will be apparent for anyone skilled in the art and shall be regarded as covered by the appended claims. It is also to be understood that the present invention is not intended to be limited to the specific examples and embodiments herein.

EXAMPLE 1

Enzymatic degradation of growth hormone

Human growth hormone preparations (CRESCORMON® and GENOTROPIN®, m22000-u) were supplied by Kabi Pharmacia AB (Stockholm, Sweden). CRESCORMON® was purified from fresh frozen human pituitaries whereas GENOTROPIN® was prepared by gene technology. TPCK-treated trypsin from bovine pancreas was obtained from Sigma (St. Louis, Mo., U.S.A.). The chromatographic materials Sephadex G100 and Sephadex G25 (PD-10) were from Pharmacia (Uppsala, Sweden). All other chemicals and solvents were of analytical grade from commercial sources.

Preparation of plasma endopeptidase

A 20 ml plasma sample collected from a non-pregnant, non-puerperal woman of fertile age, was fractionated on a Sephadex G-100 column (5 cm×90 cm). The column was eluted with 20 mM Tris-HCl, pH 7.4, and fractions of 20 ml were collected maintaining a flow rate of 80 ml/h. Aliquots (1 ml) of the fractions were desalted on Sephadex G25 (PD-10 columns) and lyophilized prior to enzyme assay. The active fractions were collected, pooled and kept frozen before further studies. Further purification was obtained by chromatography on DEAE-Sepharose CL6B. The column (2 cm×12 cm) was equilibrated with 20 mM Tris-HCl, pH 7.4, and following sample application it was eluted with a linear gradient of NaCl (0–0.5M) containing the same Tris-HCl buffer. Fractions of 10 ml were collected at a flow rate of 100 ml/h and treated as above before enzyme assay.

High performance liquid chromatography

Reversed phase HPLC was performed using a Pharmacia/LKB instrument (see F Nyberg et al J. Chromatogr. v359, 1986, p 541–551) equipped with a Spherisorb TSK-ODS-120 DT column (4.6 mm×250 mm, particle size 5µ). The column was developed with a linear gradient of acetonitrile (15–60%) containing 0.04% trifluoroacetic acid (TFA). The sample was dissolved in 200 µl of starting buffer. Fractions of 0.5 ml were collected at a flow rate of 0.5 ml/min and evaporated before receptor assay.

Enzymatic digestion

Lyophilized trypsin or plasma enzyme fractions were dissolved in 100–200 µl of 0.4M ammonium bicarbonate (pH 7.8) and incubated with 0.2–1.5 mg of human growth hormone at 37° C. for 5–8 h in a final volume of 250 µl. The reaction was terminated by the addition of 1 ml ice-cold methanol. The sample was evaporated in a Savant Vac concentrator (Hicksville, N.Y., N.Y.; U.S.A.) before further analysis by reversed phase HPLC.

Results

Figure 2:
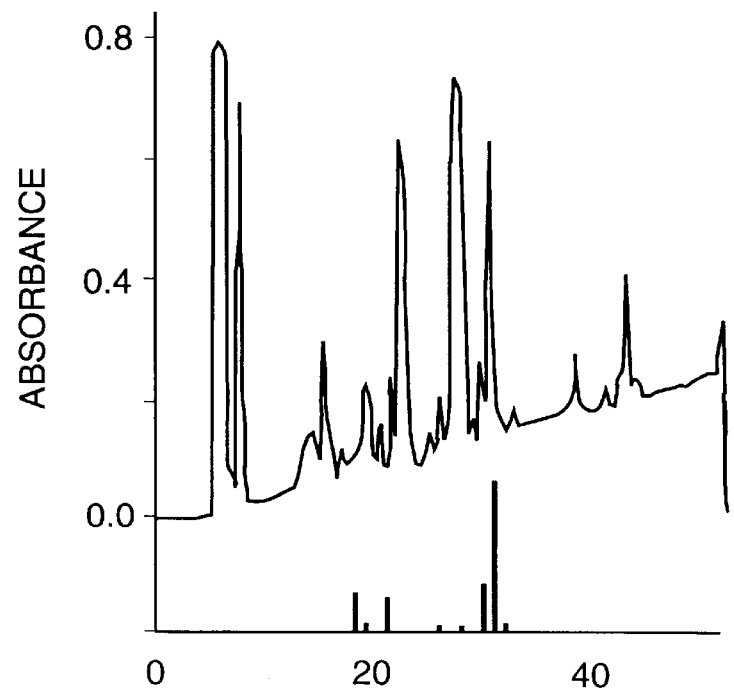
FIG. 2 shows the HPLC-pattern of receptor activity when recombinant somatropin (GENOTROPIN®) was used as a substrate for tryptic digest. The distribution of opioid receptor activity is represented by dark bars.

FIG. 1 shows a typical HPLC chromatogram of a tryptic digest of human growth hormone (CRESCORMON®). As can be seen, at least two receptor active peaks were recorded. When GENOTROPIN® was used as substrate the HPLC pattern of receptor activity showed some differences (FIG. 2). The large peak eluting in fraction 31 was still dominating. However, the peak observed in fraction 18 in the digest of the CRESCORMON® preparation, as shown in FIG. 1, was almost depleted, as shown in FIG. 2. One explanation of this may be the fact that the CRESCORMON® preparation contained a higher degree of deamidated forms of the hormone and such forms may be more susceptible to enzymatic degradation as discussed in Biochem. Biophys. Acta, v625, 1980, p255–260, F Nyberg et al. The plasma enzyme gave rise to several receptor-active fragments recorded by the EPLC-radioreceptor assay procedure. Following separation on Sephadex G-100 this enzyme was found to elute in a position corresponding to protein with a molecular mass of 100–110 ku. Further purification of the plasma enzyme was achieved by ion exchange chromatography on DEAE-Sepharose, where the enzyme eluted at a NaCl concentration of around 0.1M. The receptor-active fragments released by the plasma enzyme differed from the active tryptic fragments with regard to their behaviour in HPLC chromatography It was noted that some parts of the tryptic digest fragments of growth hormone were related to the sequence of β-casomorphin. Partial amino acid sequencing of the trypsin-released growth hormone fragments revealed that one peptide contained the Tyr-Ser-Phe-Leu-Gln SEQ. ID NO. 1 sequence.

EXAMPLE 2

Preparation of the oligopeptides according to the invention

The oligopeptides according to the invention were initially derived from the sequence Tyr-Ser-Phe-Leu-Gln as mentioned in Example 1. A number of straight and cyclic pentapeptides with the general structure Tyr-X-Phe-Leu-Z SEQ. ID NO. 1 were performed according to the following methods described in Examples 2.1 to 2.3.

EXAMPLE 2.1

Synthesis of Tyr-X-Phe-Leu-Glu SEQ. ID NO. 1

(X=Ser I, D-Ala II, Pro III)

The solid phase method was used in the standard way for the synthesis of peptides, using a Beckman 990 synthesizer. Boc amino acids were purchased from Bachem Inc. California. The phenolic group of tyrosine was protected with a 2,6-dichlorobenzyl group, the hydroxyl group of serine was protected with benzyl group and the gamma-carboxyl of glutamic acid was esterified to cyclohexylester.

At the completion of the last cycle, the peptide was cleaved from the resin and completely deprotected by treatment with anhydrous liquid HF at 0° for 60 min in the presence of anisole (30 ml HF and 3 ml anisole per gram resin). After removal of the HF and thorough drying under vacuum the resin was washed with ether and extracted with acetic acid (10%). The extracts were freeze dried. The crude peptide was purified by gel filtration on a Fractogel TSK HW-40 or PGM-2000 column with an acetic acid or trifluoroacetic acid as the eluant. The final product was obtained as a lyophilisate. Homogeneity of the peptides was judged by TCL (silica gel 60F-254 Merck; I n-BuOH/AcOH/EtOAc/Aq:1/1/1/1; II Pyridine/EtOAc/AcOH/Aq:5/5/1/3; X=Ser Rf I 0.74; Rf II 0.73) and analytical FPLC (column:pep-RPC, gradient A 0.1% TFA/Aq, B 0.1% TFA/acetoritril). The identity was established by amino acid analysis (6M HCl, 110°, 24 h) and mass spectrometric analysis, positive FAB, performed on an SX-102A double focusing masspectrometer (Jeol, Japan).

EXAMPLE 2.2

Synthesis of Tyr-Ser-Phe-Leu-Glu-NH$_2$ SEQ. ID NO. 1

This peptide was synthesized on 4-methylbenzyhydrylamine resin in exactly the same manner as described in Example 2.1. MBHA-resin (0.46 mmol/g, 1.74 g, Nova biochem Switzerland) was reacted with Boc-Glu gammacyclo hexylester. The crude peptide was purified by gelfiltration on a Fractogel TSK H W-40 column with 0.1% TFA as the eluent. TLC: Rf (I) 0.76, Rf (II) 0.79; amino acid analysis: Tyr, 0.99; Ser, 0.99; Phe, 1.01; Leu, 1.00; Glu, 0.99; FAB-MS$^m$/z 657.2 [M+H]$^+$.

EXAMPLE 2.3

Synthesis of Tyr-cyclo(-Lys-Phe-Leu-Glu-) SEQ. ID NO. 2

The synthesis was performed by solid phase technique on a 4-alcoxybenzyl alcohol resin, using the standard Fmoc strategy protocol. The α-amino functions were protected by the fluorenylmethyloxycarbonyl group, except for the α-amino function of Tyr which was protected by the benzyl oxycarbonyl group. The γ-carboxyl function of Glu, the ε-amino function of Lys and the phenolic function of Tyr were protected by benzyl, tert-butyloxycarbonyl and benzyl respectively. The peptide was cleaved from the resin by 50% trifluoroacetic acid in dichloromethane leaving all the functional groups protected except for the ε-amino function of Lys and the α-carboxyl function of Glu. Cyclization was performed in DMF at a peptide concentration of 0.1 mM by benzotriazole tetramethyluronium hexafluorophosphate (HBTU) and N-ethyldiisopropylamine. The cyclic peptide was finally deprotected by catalytic hydrogenation at atmospheric pressure in methanol with 10% Pd on charcoal as a catalyst. The peptide was characterized by amino acid analysis, HPLC, and FAB Mass spectral analysis.

EXAMPLE 3

Assays of the new oligopeptides

In a first assay, the peptide Tyr-Ser-Phe-Leu-Gln, SEQ. ID NO. 1 with a substitution of Gln for Glu, SEQ. ID NO. 1 and a shorter fragment Tyr-Gly-Leu-Leu SEQ. ID NO. 4 were synthezised with methods disclosed synthesized and used for binding studies to the $\mu$- and $\delta$-opioid receptors.

The receptor assay was performed according to Life Sci, vol. 16, 1975, p 1979ff, L Terenius et al. and Brain Res. Vol. 259, 1983, p 267–274, F Nyberg et al. using synaptic rat plasma membranes from whole rat brain without cerebellum and with $^3$H-labelled dihydromorphine as the competing radioligand. Each run included a calibration curve with Met-enkephalin and the binding activity of the tested fraction was expressed in Met-enkephalin equivalents.

Figure 3:
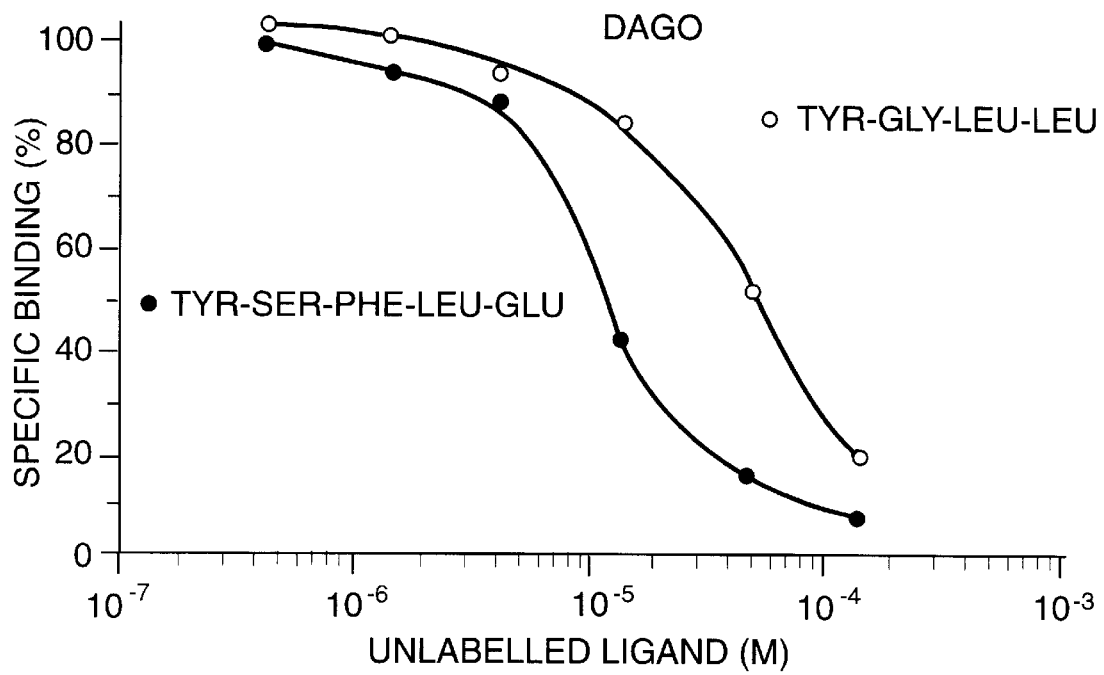
FIGS. 3 and 4 show binding studies performed according to the present invention. The figures show displacement curves for the binding of Tyr-Ser-Phe-Leu-Glu and Tyr-Gly-Leu-Leu Seq. ID No. 4 to rat membranes with ($^3$H)-DAGO (FIG. 3) and ($^3$H)-DADL (FIG. 4) as labelled ligands.
Figure 4:
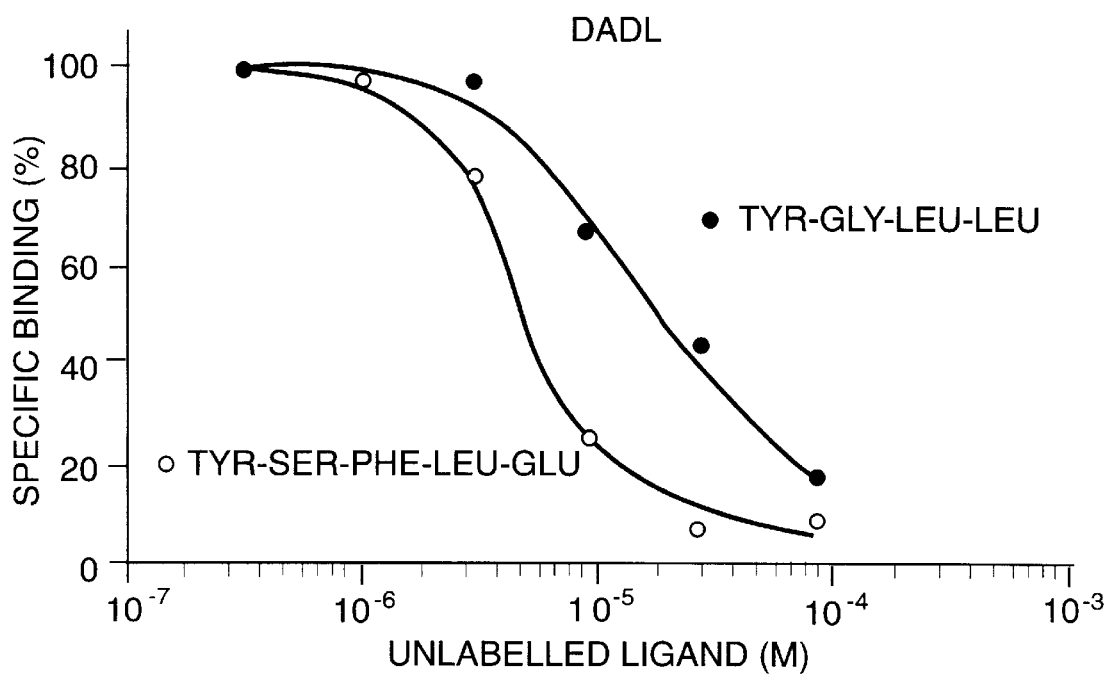

In the experiments noted in FIGS. 3 and 4 and in Table 1 ($^3$H)-(D-Ala$^2$,MePhe$^4$,Gly-ol$^5$)-enkephalin (DAGO or DAMGO) and ($^3$H)-(D-Ala$^2$,D-Leu$^5$)-enkephalin (DADL) purchased from Amersham (Buckinghamshire, England) were used as radioligands in a binding assay performed as in Reg. Peptides, Vol. 34, 1991, p169–179, E-L Glämsta et al. DAGO or DAMGO is a $\mu$-receptor ligand whereas DADL is a typical $\delta$-receptor agonist.

The calculated inhibition constants are listed in Table 1. Data indicate that the pentapeptide fragment has higher affinity for both $\mu$- and $\delta$-receptors than the shorter growth hormone fragment. The potency of Tyr-Ser-Phe-Leu-Glu SEQ. ID NO. 1 for the $\mu$-receptor was in the same order of magnitude as β-casomorphin-5 (see Table 1).

The inhibition constants, Ki, in Table 1 are defined as the concentration of the peptide that leads to a 50% blocking of the labelled ligand. In the publication β-Casomorphins and Related Peptides Ed. F Nyberg et al, pages 65–75, "Selective δ-antagonist peptides, analogues of α-casein exorphin, as probes for the opioid receptor" by S Loukas et al are various inhibiting peptides and opioid receptor activity disclosed. In Regulatory Peptides, vol 34, 1991, pages 169–179 ( E-L Glämsta et. al.) inhibition constants for β-casomorphins are disclosed.

It is thus indicated that trypsin treatment of human growth hormone results in the generation of fragments which interfere with opioid receptors. It is also evident that human plasma contains proteolytic activity which may release opioid active peptides from the hormone, which, if they pass the blood-brain barrier, may affect the central nervous system (CNS). In fact, in the clinical treatment with growth hormone some secondary effects on the CNS have been observed (unpublished). It is therefore tempting to suggest that opioid active peptide fragments released from growth hormone may reach the CNS and be responsible for these effects.

For the tests accounted for in Table 2, a number of new pentapeptides and peptides according to the prior art were manufactured in accordance with Example 2, above. The peptides were employed for both receptor tests and bioassays on electrically stimulated guinea pig ileum strips (GPI-tests). The receptor assays were performed in the same manner as above with DAMGO as a radioligand to the $\mu$-receptor. In the assays ($^3$H)-DAMGO specific binding was displaced by the different tested substances ($10^{-5}$M to $10^{-10}$M). The concentration of labelled ligand when 50% was displaced, IC$_{50}$ (inhibitory concentration), Ki and the binding capacities B$_{max}$ were calculated from a computer program (LIGAND, Biosoft, Cambridge, UK.) In the GPI-tests methods and material disclosed in Regul Pept, Vol.34, 1991, p 169–179 (E-L Glämsta et al.) and in The Hemorphins, Comprehensive Summaries of Uppsala Dissertations from the Faculty of Pharmacy 108, Acta Univers. Ups. Uppsala, 1993, E-L Glämsta, were used. The magnitude of activity in relation to a standard compound, normorphine was recorded.

Table 2 shows that inventive oligopeptides have a high binding afinity to the $\mu$-receptor. It is notable that the cyclic oligopeptides both have a high receptor affinity and a high opiate activity, suggesting a powerful agonist activity.

The straight pentapeptides according to invention also have a high receptor afinity, but a reduced biological activity as measured by the GPI-test. These tests may suggest partial agonist or a functional antagonist activity.

The differences in test value of the inhibitory constant Ki for the peptide Tyr-Ser-Phe-Leu-Glu SEQ. ID NO. 1 in Tables 1 and 2 must be credited to different analytical material and procedures at the respective condition. It is, however, to be considered that the relative magnitude of activity of different compounds in each test run is the most interesting and condusive.

The tests reveal the generation of new oligopeptides initially derived from tryptic fragments of human growth hormone have an opioid receptor affinity and an opioid activity of surprisingly high magnitude. The new compounds, consequently, show a high pharmaceutical potential and a possibility to create new tissue selective opiate receptor active pharmaceuticals with potentially reduced adverse effects.

TABLE 1

Inhibition constants of hGH fragments for ($^3$H)-DAGO and ($^3$H)-DADL binding sites in rat brain homogenates

| | Ki-Values ($\mu$M) | |
|---|---|---|
| Peptide | $^3$H)-DAGO binding site | ($^3$H)-DADL binding site |
| Tyr—Gly—Leu—Leu SEQ.ID NO. 4 | 32 | 24 |
| Tyr—Ser—Phe—Leu—Glu SEQ. ID. NO. 1 | 7.4 | 5.8 |
| Tyr—Pro—Phe—Val—Glu SEQ. ID. NO. 1 | 8.9 | — |

Binding data were obtained from inhibition experiments (duplicate determination) for determination of binding parameters by the computer program EBDA/LIGAND. A one site model was chosen (Tyr-Pro-Phe-Val-Glu=human β-casomorphine-5).

TABLE 2

| Compound | IC$_{50}$ (nM) | $^3$HDAMGO (M) × 10$^{-10}$ | K$_i$ (nM) | B$_{max}$ (pmol) | GPI-test relative activity normorphine = 1 |
|---|---|---|---|---|---|
| Tyr-Ser-Phe-Leu-Glu SEQ. ID NO.1 | 7.3 | 24.09 | 2.3 | 17.7 | <0.01 |
| Tyr-Ser-Phe-Leu-Glu-NH$_2$ SEQ. ID NO.2 | 2.6 | 24.09 | 0.82 | 72.5 | |
| Tyr-D-Ala-Phe-Leu-Glu SEQ. ID NO.1 | 0.048 | 24.01 | 0.015 | 19.7 | 0.01 |
| Tyr-Pro-Phe-Leu-Glu SEQ. ID NO.1 | 0.024 | 24.17 | 0.0067 | | 0.01 |
| Tyr-D-Ala-Phe-Leu-NH$_2$ SEQ. ID NO.1 | 0.10 | 24.02 | 0.032 | 28.3 | 0.3 |
| Tyr-D-Ala-Phe-Met-NH$_2$* | 0.15 | 24.00 | 0.047 | 14.8 | 0.5 |
| Tyr-D-Ala-Phe-Met* | 0.64 | 24.20 | 0.018 | | |
| Tyr-Cys-Phe-Leu-Cys (S—S) SEQ.ID NO.3 | 0.24 | 24.00 | 0.075 | 31.6 | 0.8 |
| Tyr-D-Cys-Phe-Leu-Cys (S—S) SEQ.ID NO.3 | 11.9 | 23.99 | 3.7 | 11.8 | |
| Tyr-Dab-Phe-Leu-Glu (cyclic) SEQ.ID NO.2 | 6.19 | 23.99 | 2.0 | 18.6 | |
| Tyr-Lys-Phe-Leu-Glu (cyclic) SEQ.ID NO.2 | 0.055 | 24.17 | 0.016 | | |

*These peptides were disclosed in U.S. Pat. No. 4,254,024

We claim:

1. Straight or cyclic pentapeptides with receptor affinity to μ or δ opioid receptors having a primary sequence backbone of Tyr-X-Phe-Leu-Z (Seq. ID Nos. 1, 2, and 3) where X and Z can be covalently coupled to provide a heterocyclic structure according to the following conditions:

i) when the pentapeptide is straight X is selected from the group consisting of Ser, Gly, Pro, AMCA and D-Ala and Z is selected from the group consisting of Glu, Gln and carboxamide derivatives of Glu or Gln (Seq. ID No. 1) with the proviso that if X is Ser, then Z is Glu or carboxamide derivatives of Glu;

ii) where the pentapeptide is cyclic X is selected from the group consisting of D- or L-2,4-diaminobutyric acid, D- or L-lysine, D- or L-ornithine and D or L-cysteine and Z is selected from the group consisting of Gln, Glu and carboxamide derivatives of Gln or Glu (Seq. ID No. 2 and 3) with the proviso that if X is D-or L-Cys, then Z is Cys (Seq. ID No. 3).

2. Pentapeptides according to claim 1 having the sequences Tyr-Ser-Phe-Leu-Glu (Seq. ID No. 1), Tyr-Ser-Phe-Leu-Glu-NH$_2$ (Seq. ID No. 1), Tyr-D-Ala-Phe-Leu-Glu (Seq. ID No. 2), Tyr-D-Ser-Phe-Leu-Glu (Seq. ID No. 1), Tyr-Pro-Phe-Leu-Glu (Seq. ID No. 1), or Tyr-AMCA-Phe-Leu-Glu (Seq. ID No. 1).

3. Pentapeptides according to claim 1 having the sequences:
Tyr-cyclo(-N⁴-2,4-D-diaminobutyric acid-Phe-Leu-Gln-) (Seq. ID No. 2),
Tyr-cyclo(-N⁴-2,4-L-diaminobutyric acid-Phe-Leu-Gln-) (Seq. ID No. 2),
Tyr-cyclo(-N⁴-2,4-D-diaminobutyric acid-Phe-Leu-Glu-) (Seq. ID No. 2),
Tyr-cyclo(-N⁴-2,4-L-diaminobutyric acid-Phe-Leu-Glu-) (Seq. ID No. 2),
Tyr-cyclo(-D-Lys-Phe-Leu-Glu-) (Seq. ID No. 2), Tyr-cyclo(-D-Orn-Phe-Leu-Glu-) (Seq. ID No. 2),

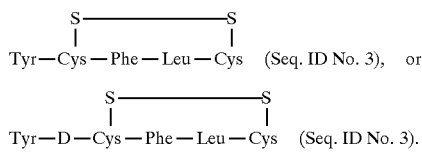
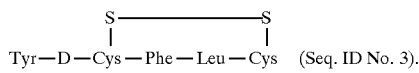

4. A pharmaceutical composition comprising at least one of the oligopeptides claim 1 and suitable carriers and/or diluents for adapting it to an appropriate administration route.

5. A method for manufacturing a preparation for alleviating pain, treating depression, treating opioid addition, and providing comfort to individuals suffering from stress or shock, said method comprising the step of:
constructing straight or cyclic pentapeptides with receptor affinity to μ or δ opioid receptors having a primary sequence backbone of Tyr-X-Phe-Leu-Z (Seq. ID Nos. 1, 2, and 3) where X and Z can be covalently coupled to provide a heterocyclic structure according to the following conditions:
i) when the pentapeptide is straight X is selected from the group consisting of Ser, Gly, Pro, AMCA and D-Ala and Z is selected from the group consisting of Glu, Gln and carboxamide derivatives of Glu or Gln, Seq. ID No. 1;
ii) where the pentapeptide is cyclic X is selected from the group consisting of D- or L-2,4-diaminobutyric acid, D- or L-lysine, D- or L-ornithine and D or L-cysteine and Z is selected from the group consisting of Gln, Glu and carboxamide derivatives of Gln or Glu (Seq. ID No. 2 and 3) with the proviso that if X is D-or L-Cys, then Z is Cys (Seq. ID No. 3); and where when the pentapeptide is straight, if X is Ser, then Z is Glu or carboxamide derivatives of Glu.

6. The method according to claim 5, wherein the pentapeptide is selected from the group consisting of the sequences Tyr-Ser-Phe-Leu-Glu (Seg. ID No. 1), Tyr-Ser-Phe-Leu-Glu-NH₂Seq. ID No. 1), Tyr-D-Ala-Phe-Leu-Glu (Seq. ID No. 1), Tyr-D-Ser-Phe-Leu-Glu (Seq. ID No. 1), Tyr-Pro-Phe-Leu-Glu (Seq. ID No. 1), and Tyr-AMCA-Phe-Leu-Glu (Seg. ID No. 1).

7. The method according to claim 5, wherein the pentapeptide is selected from the group consisting of the sequences:
Tyr-cyclo(-N⁴-2,4-D-diaminobutyric acid-Phe-Leu-Gln-) (Seq. ID No. 2),
Tyr-cyclo(-N⁴-2,4-L-diaminobutyric acid-Phe-Leu-Gln-) (Seq. ID No. 2),
Tyr-cyclo(-N⁴-2,4-D-diaminobutyric acid-Phe-Leu-Glu-) (Seq. ID No. 2),
Tyr-cyclo(-N⁴-2,4-L-diaminobutyric acid-Phe-Leu-Glu-) (Seq. ID No. 2),
Tyr-cyclo(-D-Lys-Phe-Leu-Glu-) (Seq. ID No. 2), and Tyr-cyclo(-D-Orn-Phe-Leu-Glu-) (Seq. ID No. 2),

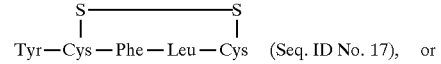
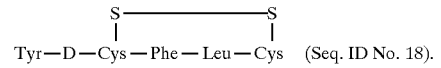

8. A method for treatment of pain, depression, opioid addition, stress or shock, the method comprising the step of:
administering to a patient in need of such treatment an effective amount of a straight or cyclic pentapeptide with receptor affinity to μ or δ opioid receptors having a primary sequence backbone of Tyr-X-Phe-Leu-Z (Seq. ID Nos. 1, 2, and 3) where X and Z can be covalently coupled to provide a heterocyclic structure according to the following conditions:
i) when the pentapeptide is straight X is selected from the group consisting of Ser, Gly, Pro, AMCA and D-Ala and Z is selected from the group consisting of Glu, Gln and carboxamide derivatives of Glu or Gln, Seq. ID No. 1;
ii) where the pentapeptide is cyclic X is selected from the group consisting of D- or L-2,4-diaminobutyric acid, D- or L-lysine, D- or L-ornithine and D or L-cysteine and Z is selected from the group consisting of Gln, Glu and carboxamide derivatives of Gln or Glu (Seq. ID No. 2 and 3) with the proviso that if X is D-or L-Cys, then Z is Cys (Seq. ID No. 3).

* * * * *